United States Patent

Clark et al.

[11] Patent Number: 5,167,725
[45] Date of Patent: Dec. 1, 1992

[54] TITANIUM ALLOY BLADE COUPLER COATED WITH NICKEL-CHROME FOR ULTRASONIC SCALPEL

[75] Inventors: Richard J. Clark, Norfolk; Dale E. Whipple, Taunton, both of Mass.; Alan E. Thomas, Ocean City, N.J.

[73] Assignee: Ultracision, Inc., Smithfield, R.I.

[21] Appl. No.: 561,092

[22] Filed: Aug. 1, 1990

[51] Int. Cl.$^5$ .............................. C23C 14/00
[52] U.S. Cl. .................. 428/680; 148/427; 606/169; 606/79; 606/53; 228/195; 427/427
[58] Field of Search ............ 148/4, 20.3, 144, 148, 148/427; 606/79, 53, 169; 428/662, 680, 679; 228/195

[56] References Cited

U.S. PATENT DOCUMENTS

| | | | |
|---|---|---|---|
| 3,761,372 | 9/1973 | Sastri | 204/192 |
| 3,761,373 | 9/1973 | Sastri | 204/192 |
| 3,761,374 | 9/1973 | Bromer et al. | 204/192 |
| 3,900,636 | 8/1975 | Curry et al. | 427/38 |
| 3,911,579 | 10/1975 | Lane et al. | 30/346.54 |
| 3,915,757 | 10/1975 | Engel | 148/6 |
| 4,122,239 | 10/1978 | Riboulet et al. | 428/680 |
| 4,122,602 | 10/1978 | Sastri et al. | 30/346.5 |
| 4,188,952 | 2/1980 | Loschilov et al. | 606/169 |
| 4,736,743 | 4/1988 | Daikuzono | 128/303.1 |
| 4,770,067 | 9/1988 | Liu et al. | 76/104 R |
| 4,832,979 | 5/1989 | Hoshino | 427/38 |

FOREIGN PATENT DOCUMENTS

| | | | |
|---|---|---|---|
| 2202015 | 7/1972 | Fed. Rep. of Germany | 148/4 |
| 0033474 | 4/1981 | Japan | 148/20.3 |
| 0136972 | 10/1981 | Japan | 148/20.3 |

OTHER PUBLICATIONS

Shoemaker, R. H. "New Surface Treatments for Titanium" 1972 Titanium Science & Technology pp. 2501-2516.

"Surface Modification . . ." Mat. Sci. & Engineering pp. 373-380.

Primary Examiner—R. Dean
Assistant Examiner—Sikyin Ip
Attorney, Agent, or Firm—Nixon & Vanderhye

[57] ABSTRACT

Ultrasonic blade coupler comprising a blade element composed of a material selected from aluminum and titanium rendered sharpenable by a surface hardening treatment. The blade coupler exhibits improved acoustical properties with reduced energy consumption.

8 Claims, 1 Drawing Sheet

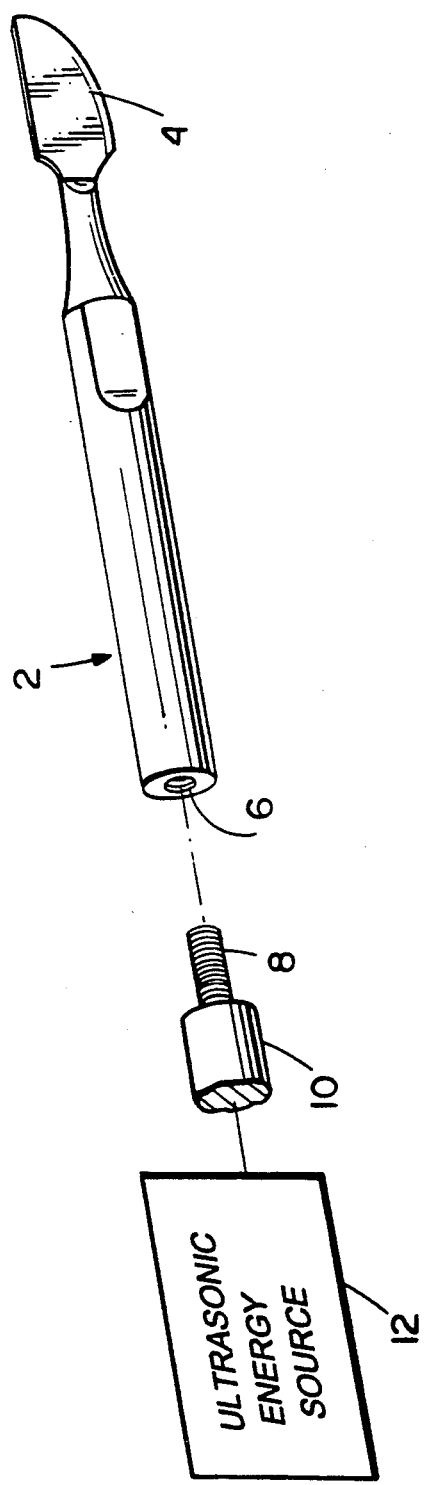

TITANIUM ALLOY BLADE COUPLER COATED WITH NICKEL-CHROME FOR ULTRASONIC SCALPEL

The present invention relates generally to an utlrasonic blade coupler having improved ultrasonic energy transmission properties.

BACKGROUND OF THE INVENTION

It is well known to employ ultrasonic surgical devices for performing surgical procedures. Generally speaking, those surgical devices are hand-held instruments connected to a source of ultrasonic energy. The ultrasonic energy is transmitted through a connection or mount between the ultrasonic energy source and a hand-held coupler which mounts the surgical tool, for example a surgical blade mounted at the tip of the coupler. This facilitates transmission of ultrasonic energy from the ultrasonic energy source through the coupler to the surgical blade to generate ultrasonic vibrations in the blade.

In the past, cutting edges have been fabricated from stainless steel since stainless steel can be sharpened and honed to a fine edge. However, the use of stainless steel blades in ultrasonic applications has certain associated problems. In particular, stainless steel absorbs ultrasonic energy, so that additional energy has to be supplied to the blade to obtain the desired displacement. The supply of this additional energy results in heat generation which is wasteful of energy and undesirable in surgical applications.

SUMMARY OF THE INVENTION

It has now been discovered, according to the present invention, that improved ultrasonic blade couplers may be fabricated from aluminum or titanium which has been subjected to a surface hardening treatment to facilitate sharpening to form a cutting edge. Aluminum and titanium are particularly suited to this purpose since those two materials do not absorb ultrasonic energy to the same extent as stainless steel.

According to one aspect of the present invention, there is provided an ultrasonic blade coupler comprising means for mounting the coupler to a source of ultrasonic energy and a blade element formed from a material selected from aluminum and titanium which has been hardened to facilitate the formation of a cutting edge on the blade element.

According to another aspect of the present invention, there is provided a method of producing an ultrasonic blade coupler, comprising the steps of providing a blade coupler having a blade element formed from a material selected from aluminum and titanium and hardening the material to facilitate the formation of a cutting edge on the blade element.

The aluminum or titanium ultrasonic blade coupler of the invention exhibits excellent performance characteristics when used for surgical applications. In particular, the blade coupler exhibits lower absorption of ultrasonic energy than stainless steel blade couplers so that a given longitudinal displacement is obtained using less power than for a comparable stainless steel blade coupler, and less heat is generated. The blade couplers of the invention are, therefore, particularly well suited for surgical application in view of the reduced heat generation, and are also more economical in use as a result of reduced power consumption.

BRIEF DESCRIPTION OF THE DRAWING

The invention will now be described in more detail with reference to the accompanying Figure which shows a blade coupler of the invention.

DETAILED DESCRIPTION OF THE INVENTION

In the following description, it is to be understood that the term "blade element" refers not only to a scalpel-like cutting knife but also to other cutting or severing devices but not limited to, bone chisels, orthopaedic instruments such as meniscus severing instruments for use in arthroscopic surgery, and other surgical instruments for cutting hard and soft tissue.

Referring to the Figure, there is shown a blade coupler, generally referenced 2, having a blade element 4 at one end and means at the other end for connecting the coupler to an accoustical mount. In the embodiment shown in the Figure, the blade coupler 2 is provided with an internally threaded bore 6 at the end opposite to that carrying the blade element 4, which is threaddedly engageable with an externally threaded projection 8 of an acoustical mount 10. It will be appreciated, however, that this connecting arrangement may be reversed so that the blade coupler is provided with an externally threaded projection and the acoustical mount is provided with a corresponding internally threaded bore. The acoustical mount 10, in turn, is coupled to an ultrasonic energy source 12, whereby ultrasonic energy is provided to the blade element 4.

The blade coupler 2 is comprised of a material selected from aluminum and titanium. Before an edge can be formed, it is necessary to harden the surface of the blade to a depth sufficient to allow an edge to be produced. Standard 440C stainless steel blades have a hardness in the range of Rockwell 58-C to 62-C. In the present invention, an acceptable surgical edge is achieved with a hardness of at least Rockwell 40-C. It will be appreciated, however, that the harder the material, the less chance there is of the cutting edge rolling over as it becomes increasingly thinner, and thus a sharper blade may be produced.

Numerous hardening treatments can be employed for this purpose. Preferred treatments are described below.

For both aluminum and titanium, ion implantation may be employed. Ion implantation only produces a "hard" surface (at least a surface hardness of 800 to 1300 Vickers, for example 800 to 900 Vickers) to a depth of approximately 0.5 microns. Therefore, ion implantation is suitable only for increasing durability where a "sharp" edge has already been produced. Typical surface hardness values are given below:

| Material | Surface Hardness: Knoop Scale |
| --- | --- |
| Titanium | 380 |
| Quartz | 800 |
| Sapphire | 1000 |
| Titanium Nitride | 1300 |
| Natural Diamond | 8000–12000 |

There is no exact conversion between the Knoop Scale (surface hardness) and the Rockwell Scale (gross hardness). For example, Titanium Ti-6Al-4V has a Rockwell hardness of 33-C.

Ion implantation results in the formation of wear resistant alloys in the surface of the blade. Generally, the process is performed at temperatures below 300° F. to minimize the risk of distortion or bulk property changes in the blade coupler. An advantage of this particular approach is that no coating is formed on the blade which might change the dimensions of the blade or flake or chip off which would be extremely undesirable from a surgical standpoint. Moreover, once the alloy has been produced in the surface of the blade, there is no need for subsequent grinding, heat treating, straightening or polishing.

In the ion implantation process, atoms of a desired elemental species, such as nitrogen or chromium, are accelerated to very high velocities in a small particle accelerator and injected into the surface of the metal. Because of the very high kinetic energy, the accelerated ions are able to penetrate into and form alloys and structures in the surfaces of the metal which cannot be formed by conventional thermometal alloying processes.

Details of the ion implantation process which may be used to produce the blade coupler of the invention appear, for example, in Sioshansi, P., Ion Beam Modification of Materials for Industry, Metallurgical and Protective Coatings, Thin Solid Films, 118, 61–71 (1984), and Sioshansi, P., Surface Modification of Industrial Components by Ion Implantation, Materials Science Engineering, 90, 373–383 (1987), the disclosures of which are hereby incorporated by reference.

Another hardening method is hard-facing or "deep nitriding". One such process for titanium is the Tiduran process which employs a molten salt bath to produce a nitriding effect to a depth of about 0.002 inches. The Tiduran process is described in detail in Shoemaker, R. H., New Surface Treatments for Titanium, Titanium Science and Technology, 2501–2516 (1972).

Gas nitriding is yet another method which can be used. However, the high temperatures associated with this process tend to distort the substrate being treated, and are not suitable for low melting point materials such as aluminum.

A further hardening method is "hard-facing", which is done either by spraying or welding a hard coating onto the surface to produce a hard edge for sharpening. With reference to the spraying technique, one hard-facing material is tungsten carbide which is made of tungsten carbide nodules in a cobalt and tungsten carbide matrix. However, the hard nodules of tungsten carbide in this material have a tendency to "break out" of the matrix, thereby preventing the formation of a sharp edge. To alleviate this situation, homogeneous materials such as an alloy of 80% nickel and 20% chromium may be employed. By "homogeneous material" is meant a material characterized by the substantial absence of a matrix or discrete zones of different elements or compounds within the material. With these hard materials, there is no need to subject the blade to a further hardening treatment after sharpening, although they can be treated if so desired.

The other method of hard-facing is to weld a hardenable material onto the substrate to produce a weld-overlay. It has been found according to the invention that better results are obtained when the hard material is welded to titanium than to aluminum. Referring to titanium, it is possible, for example, to weld a hardenable titanium alloy such as Beta-C(Ti-3Al-8V-6Cr-4Mo-4Zr) or Ti-6Al-2Sn-4Zr-6Mo, to a Ti-6Al-4V ELI substrate. The resulting combination has been successfully welded and sharpened to provide a good sharp edge.

Weld-brazing is a further technique which may be used. For example, a blade coupler exhibiting good acoustical properties and superior sharpenability is formed when stainless steel, preferably 440C stainless steel, is braze-welded to a titanium blade coupler.

EXAMPLES

The invention will now be described with reference to the following non-limiting examples.

EXAMPLE 1

Base Material: Titanium, Ti-6Al-4V-ELI Thermal Spray Coating: Nickel-Chrome

In this Example, the blade coupler employed was composed of a base material of an Alpha-Beta alloy of titanium comprising 6% aluminum and 4% vanadium with the remainder being titanium and several trace elements. While other alloys of titanium may be used, this particular alloy has good strength, good fatigue resistance and is the choice for medical implants (ASTM F136). The alloy is also acoustically active. The ELI (extra low interstitial) grade has a lower permissible oxygen (and hydrogen) content which is specified primarily for welding applications to prevent brittle welds. The ELI garde also possesses good fatigue resistance which makes it particularly suitable for application to ultrasonic blade couplers.

A spray coating process which may be used is the Union Carbide "D Gun" process. The process employs a "gun" which mixes oxygen and a fuel, such as acetylene, in a chamber and then ignites it in an explosive manner. The resultant high velocity gases carry the nickel-chromium power to the substrate. It is this high velocity, along with the partial melting of the nickel-chromium, which produces the high( >10,000 PSI) bond strength needed to withstand the grinding operation employed for sharpening and also to withstand the ultrasonic excitation.

The spray coating producing particularly good blade sharpenability was one based on a homogeneous alloy composed of 80% nickel and 20% chromium. The resulting spray-coated material had a hardness of Rockwell 48C (in excess of the approximately Rockwell 40C minimum generally agreed to be required for grinding a reasonable edge) and a minimum bond strength between the base material and the coating of 10,000 PSI. The resulting blade coupler exhibited good acoustical properties and good blade sharpenability.

EXAMPLE 2

Base Material: Aluminum 7075-T6 Thermal Spray Coating: Nickel-Chrome

The blade coupler in this Example was composed of a high strength "aircraft grade" aluminum with excellent acoustic properties and a Brinell hardness of 150 (below Rockwell 40C). Aluminum 7075 is composed of 5.6% zinc, 2.5% magnesium, 1.6% copper and 0.23% chromium with the remainder being aluminum. The "T" in the 7075-T6 applies to products which are thermally treated, with or without supplementary strain hardening, to produce stable tempers. "T6" is defined as: solution heat treated and then artificially aged and applies to products that are not cold-worked after solution heat treatment, or in which the effect of cold work in flattening or straightening may not be recognized in mechanical property limits. Other conditions, such as "T7" (solution heat treated and stabilized) are also suitable for this application. Thus, the application is not limited to aluminum subjected to T6 heat treatment.

The spray coating was the same as in Example 1. The resulting blade coupler exhibited excellent acoustical properties with good blade sharpenability.

EXAMPLE 3

Base Material: Titanium Ti-6Al-4V ELI Weld Overlay: Titanium Ti-3Al-8V-6Cr-4Zr-4Mo ("Beta-C")

The base material for the blade coupler in this Example was the same as that in Example 1.

The weld overlay was a Beta alloy of titanium containing 3% aluminum, 8% vanadium, 6% chromium, 4% zirconium and 4% molybdenum along with trace elements. In the as welded and quenched form the Beta-C has a hardness of Rockwell C42. This higher hardness resulted in a blade coupler possessing good acoustical properties as well as improved sharpenability of the edge. Bond strength was not a critical factor since the welding produced a "metallurgical" bond.

A TIG (Tungsten Inert Gas) welding process is used to melt the Beta-C onto the Ti-6Al-4V ELI. The two materials are "melted" together at their interface with a subsequent melding of their properties. However, at the point where the edge is ground, the Beta-C remains in its virgin state retaining its original properties. Upon quenching the "weld" (with the shield gas), the Beta-C takes on a microstructure that produces the hardness required.

EXAMPLE 4

Base Materials: Titanium Ti-6Al-4V ELI or Aluminum 7075-T6, with a Nitrided edge to retain sharpness Two blade couplers were used in this Example in which the base materials were the same as in Examples 1 and 2. Nitriding brings the surface hardness levels to the 800–900 Vickers (approximately Rockwell C60-C70).

The nitrided layer can be produced by several processes including ion implantation, which produces a 0.5 micron thick layer and requires the edge to be established before nitriding, or by use of a molten salt bath, or gas nitriding, which produces 0.0005" to 0.002" thick layers. Grinding the edge after nitriding may optionally be carried out. Ion implantation has the advantage of being carried out at lower temperatures and thus avoids potential distortion of the blade coupler.

EXAMPLE 5

Base Material: Titanium Ti-6Al-4V ELI Brazed to 440C Stainless Steel

The blade coupler in this Example employed the same base material as in Example 1 above, thereby utilizing the good acoustic properties of titanium while having a hard material (440C, Rockwell 60C) for the edge. The titanium can be nickel-plated and then brazed in air or unplated titanium can be brazed in a vacuum or an inert atmosphere, according to conventional techniques. 440C is a martensitic stainless steel which is a standard in the industry as a surgical scalpel blade. Presharpened 440C blades are readily available in standard and custom configurations.

Several brazing alloys are available including, for example, 56% silver-22% copper-17% zinc-5% tin, 90% silver-10% palladium, and 80% gold-20% palladium.

An additional technique is to "weld-braze" the two materials using an electric arc using the TIG process mentioned above in Example 3. The titanium is "melted over" onto the 440C without actually mixing the two materials, which mixing is known to cause carbide precipitation and potential cracking problems.

EXAMPLE 6

Base Material: Titanium Ti-6Al-4V-ELI or Aluminum 7075-T6 Thermal Spray Coating: Nickel-Chrome, with a Nitrided edge to retain sharpness This Example describes a preferred embodiment consisting of spray-coating blade couplers in which the base material is as in Examples 1 and 2, with a nitrided edge as in Example 4.

We claim:

1. An ultrasonic blade coupler, comprising:
   mounting means at one end of the blade coupler for mounting the blade coupler to an ultrasonic energy source; and
   a blade element at an other end of the blade coupler comprising a titanium alloy comprising about 6 weight % aluminum and about 4 weight % vanadium and the remainder titanium and trace elements, said blade element being coated with nickel-chrome, to thereby render it sharpenable.

2. A blade coupler according to claim 1, wherein said nickel-chrome comprises about 80% by weight nickel and 20% by weight chromium.

3. A blade coupler according to claim 1, wherein said material further comprises a weld overlay of titanium Ti-3Al-8V-6Cr-4Zr-4Mo.

4. A blade coupler according to claim 3, wherein said weld overlay comprises by weight about 3% aluminum, about 8% vanadium, about 6% chromium, about 4% zirconium and about 4% molybdenum with trace elements, and the remainder titanium.

5. A blade coupler according to claim 1, wherein said nickel-chrome coating has a nitrided edge.

6. A blade coupler according to claim 1, wherein said material has a surface hardness is in the range of 800 to 1300 Vickers.

7. A blade coupler according to claim 6, wherein said hardness is in the range of 800 to 900 Vickers.

8. A method for producing an ultrasonic blade coupler, said method comprising the steps of:
   providing a blade coupler having a blade element comprising a titanium alloy comprising about 6 weight % aluminum and about 4 weight % vanadium and the remainder titanium and trace elements; and
   coating said blade element with nickel-chrome to facilitate a formation of a sharpenable cutting edge on the blade element.

* * * * *